US00PP18622P2

(12) United States Plant Patent
Dümmen

(10) Patent No.: US PP18,622 P2
(45) Date of Patent: Mar. 18, 2008

(54) POINSETTIA PLANT NAMED 'DUEMETRO'

(50) Latin Name: *Euphorbia pulcherrima*
Varietal Denomination: Duemetro

(75) Inventor: Tobias Dümmen, Rheinberg (DE)

(73) Assignee: Dümmen Jungpflanzen, Rheinberg (DE)

( * ) Notice: Subject to any disclaimer, the term of this patent is extended or adjusted under 35 U.S.C. 154(b) by 0 days.

(21) Appl. No.: 11/591,013

(22) Filed: Nov. 1, 2006

(51) Int. Cl.
*A01H 5/00* (2006.01)

(52) U.S. Cl. ..... Plt./307

(58) Field of Classification Search ..... Plt./307
See application file for complete search history.

(56) References Cited

PUBLICATIONS

UPOV ROM GTITM Computer Database, GTI Jouve Retrieval Software 2007/02 Citations for 'Duemetro'.*

* cited by examiner

*Primary Examiner*—Wendy Haas
(74) *Attorney, Agent, or Firm*—C. A. Whealy

(57) ABSTRACT

A new and distinct cultivar of Poinsettia plant named 'Duemetro', characterized by its upright and outwardly spreading plant habit; freely branching habit; early flowering habit; inflorescences with red-colored flower bracts; excellent post-production longevity; and resistance to *Botrytis*.

1 Drawing Sheet

Botanical designation: *Euphorbia pulcherrima.*
Cultivar denomination: 'Duemetro'.

BACKGROUND OF THE INVENTION

The present invention relates to a new and distinct cultivar of Poinsettia plant, botanically known as *Euphorbia pulcherrima* Willd., and hereinafter referred to by the name 'Duemetro'.

The new Poinsettia a product of a planned breeding program conducted by the Inventor in Rheinberg, Germany. The objective of the breeding program is to create new freely branching Poinsettia cultivars with attractive floral bract coloration and excellent post-production longevity.

The new Poinsettia originated from a cross-pollination made by the Inventor in October, 1999 of a proprietary selection of *Euphorbia pulcherrima* Willd. identified as code number 95-752-001, not patented, as the female, or seed, parent, with a proprietary selection of *Euphorbia pulcherrima* Willd. identified as code number E-005-24, not patented, as the male, or pollen, parent. The cultivar Duemetro was discovered and selected by the Inventor as a single flowering plant within the progeny of the stated cross-pollination in a controlled environment in Rheinberg, Germany in December, 2003.

Asexual reproduction of the new Poinsettia by terminal vegetative cuttings in a controlled environment in Rheinberg, Germany since December, 2003, has shown that the unique features of this new Poinsettia are stable and reproduced true to type in successive generations of asexual reproduction.

SUMMARY OF THE INVENTION

The cultivar Duemetro has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Duemetro'. These characteristics in combination distinguish 'Duemetro' as a new and distinct cultivar of Poinsettia:

1. Upright and outwardly spreading plant habit.
2. Freely branching habit.
3. Early flowering habit.
4. Inflorescences with red-colored flower bracts.
5. Relatively large cyathia.
6. Excellent post-production longevity.
7. Resistance to *Botrytis.*

In side-by-side comparisons conducted in Rheinberg, Germany, plants of the new Poinsettia differed from plants of the female parent selection in the following characteristics:

1. Plants of the new Poinsettia were more compact than plants of the female parent selection.
2. Plants of the new Poinsettia had more cyathia per inflorescence than plants of the female parent selection.

In side-by-side comparisons conducted in Rheinberg, Germany, plants of the new Poinsettia differed from plants of the male parent selection in the following characteristics:

1. Plants of the new Poinsettia and the male parent selection differed in flower bract shape.
2. Plants of the new Poinsettia had more cyathia per inflorescence than plants of the male parent selection.

Plants of the new Poinsettia can be compared to plants of the Poinsettia cultivar Fiscor, disclosed in U.S. Plant Pat. No. 9,364. In side-by-side comparisons conducted in Rheinberg, Germany, plants of the new Poinsettia differed from plants of the cultivar Fiscor in the following characteristics:

1. Plants of the new Poinsettia were larger than plants of the cultivar Fiscor.
2. Plants of the new Poinsettia had longer internodes than plants of the cultivar Fiscor.

3. Plants of the new Poinsettia had larger inflorescences than plants of the cultivar Fiscor.
4. Plants of the new Poinsettia had larger flower bracts than plants of the cultivar Fiscor.
5. Plants of the new Poinsettia had larger cyathia than plants of the cultivar Fiscor.

BRIEF DESCRIPTION OF THE PHOTOGRAPH

The accompanying photograph illustrates the overall appearance of the new Poinsettia. These photograph shows the colors as true as it is reasonably possible to obtain in colored reproductions of this type. Colors in the photograph may differ slightly from the color values cited in the detailed botanical description which accurately describe the colors of the new Poinsettia. The photograph comprises a side perspective view of a typical flowering plant of 'Duemetro' grown in a container.

DETAILED BOTANICAL DESCRIPTION

In the following description, color references are made to The Royal Horticultural Society Colour Chart, 1995 Edition, except where general terms of ordinary dictionary significance are used. The aforementioned photograph and following observations and measurements describe plants grown in Rheinberg, Germany during the winter in a glass-covered greenhouse and under conditions and practices which approximate those generally used in commercial Poinsettia production. During the production of the plants, day and night temperatures averaged 22° C. and light levels were about 4,500 lux. Measurements and numerical values represent averages for typical flowering plants. Single plants were grown in 13-cm containers and pinched one time. Plants were about 16 weeks old when the photographs and the detailed description were taken.

Botanical classification: *Euphorbia pulcherrima* cultivar Duemetro.

Parentage:

*Female, or seed, parent.*—Proprietary selection of *Euphorbia pulcherrima* Willd. identified as code number 95-752-001, not patented.

*Male, or pollen, parent.*—Proprietary selection of *Euphorbia pulcherrima* Willd. identified as code number E-005-24, not patented.

Propagation:

*Type.*—Terminal vegetative cuttings.

*Time to initiate roots, summer.*—About nine days at 22° C.

*Time to initiate roots, winter.*—About 13 days at 22° C.

*Time to produce a rooted young plant, summer.*—About three weeks at 22° C.

*Time to produce a rooted young plant, winter.*—About four weeks at 22° C.

*Root description.*—Fibrous, fleshy; white in color.

*Rooting habit.*—Freely branching; dense.

Plant description:

*Plant habit and form.*—Upright and outwardly spreading plant habit; inverted triangle. Inflorescences positioned above the foliar plane. Moderately vigorous growth habit.

*Plant height.*—About 30 cm.

*Plant diameter or spread.*—About 41.5 cm.

*Lateral branch description.*—Quantity: Freely branching habit, about four to five lateral branches develop after pinching. Length: About 21.5 cm. Diameter: About 5.5 mm. Internode length: About 1.7 cm to 1.8 cm. Strength: Strong. Texture: Smooth, glabrous. Color: 137A.

*Foliage description.*—Arrangement: Alternate, simple. Length: About 12.2 cm. Width: About 7.9 cm. Shape: Ovate. Apex: Apiculate. Base: Obtuse. Margin: Lobed; dentate. Venation pattern: Pinnate. Texture, upper and lower surfaces: Smooth, glabrous. Color: Developing foliage, upper surface: 137A. Developing foliage, lower surface: 138A. Fully expanded foliage, upper surface: 139A; venation, 146B. Fully expanded foliage, lower surface: 137A to 137B; venation, 146B to 146C. Petiole: Length: About 6.1 cm. Diameter: About 2.3 mm. Texture, upper and lower surfaces: Smooth, glabrous. Color, upper and lower surfaces: 187A to 187B.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent. Inflorescences positioned above the foliage.

*Natural flowering season.*—Autumn/winter; inflorescence initiation and development is induced under long nyctoperiod conditions. Early flowering, response time is about eight weeks.

*Post-production longevity.*—Excellent post-production longevity; plants of the new Poinsettia maintain good substance and bract color for about two months under interior conditions.

*Inflorescence size.*—Diameter: About 30.7 cm. Height (depth): About 5.5 cm.

*Flower bracts.*—Quantity per inflorescence: About 15. Length: About 15.7 cm. Width: About 10 cm. Shape: Ovate; slightly lobed. Apex: Apiculate. Base: Obtuse. Margin: Entire; slightly lobed. Texture, upper and lower surfaces: Smooth, glabrous. Venation pattern: Pinnate. Color: Developing or transitional bracts, upper surface: 46A. Developing or transitional bracts, lower surface: 53B. Fully developed bracts, upper surface: 46A to 46B; color becoming closer to 46C to 46D with development. Fully developed bracts, lower surface: 46C to 46D. Venation, upper and lower surfaces: Similar to flower bract color. Bract petiole: Length: About 2.4 cm. Diameter: About 2 mm. Texture, upper and lower surfaces: Smooth, glabrous. Color, upper and lower surfaces: 53A to 53B.

*Cyathia.*—Quantity per corymb: About ten to twelve. Diameter of cyathia cluster: About 3 cm. Length: About 9.7 mm. Width: About 6 mm. Shape: Ovoid. Color, immature: 143B. Color, mature: 143B to 143C. Nectaries: Quantity per cyathium: About one or two. Size: About 4.7 mm. Color: 17A.

*Peduncles.*—Length: About 4 mm. Diameter: About 1.25 mm. Strength: Strong to moderately strong. Texture: Smooth, glabrous. Color: 143C.

*Reproductive organs.*—Stamens: Quantity per cyathium: About ten. Anther shape: Oval. Anther length: About 0.5 mm. Anther color: 187A. Amount of pollen: Abundant. Pollen color: 9A. Pistils: Quantity per cyathium: One. Pistil length: About 1 cm. Style length: About 2 mm. Style color: 144B. Stigma shape: Crested. Stigma color: 59A to 59B. Ovary color: 144A. Seed/fruit: Seed and fruit production has not been observed.

Disease/pest resistance: Plants of the new Poinsettia have been shown to be resistant to *Botrytis*. Plants of the new Poinsettia have not been shown to be resistant to pests and other pathogens common to Poinsettias.

Temperature tolerance: Plants of the new Poinsettia have been observed to tolerate temperatures ranging from about 12° C. to about 40° C.

It is claimed:

1. A new and distinct Poinsettia plant named 'Duemetro' as illustrated and described.

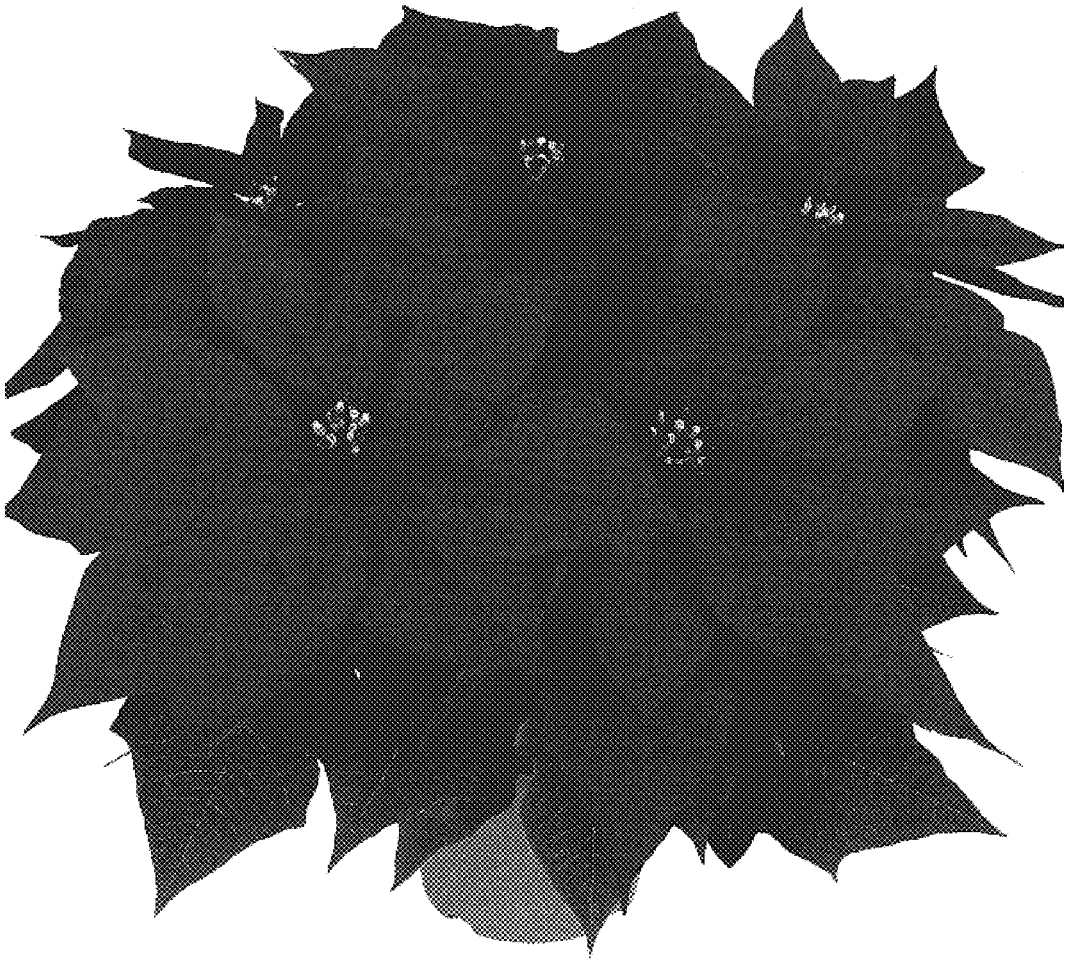

* * * * *